(12) United States Patent
Sakaue et al.

(10) Patent No.: US 7,091,017 B2
(45) Date of Patent: Aug. 15, 2006

(54) FRUCTOSYL AMINO ACID OXIDASE

(75) Inventors: Ryoichi Sakaue, Chiba (JP); Naoki Kajiyama, Chiba (JP)

(73) Assignee: Kikkoman Corporation, Noda (JP)

( * ) Notice: Subject to any disclaimer, the term of this patent is extended or adjusted under 35 U.S.C. 154(b) by 326 days.

(21) Appl. No.: 10/416,537

(22) PCT Filed: Nov. 21, 2001

(86) PCT No.: PCT/JP01/10167

§ 371 (c)(1),
(2), (4) Date: May 28, 2003

(87) PCT Pub. No.: WO02/44387

PCT Pub. Date: Jun. 6, 2002

(65) Prior Publication Data

US 2004/0115662 A1    Jun. 17, 2004

(30) Foreign Application Priority Data

Nov. 28, 2000 (JP) .............................. 2000-360590
Aug. 10, 2001 (JP) .............................. 2001-243049

(51) Int. Cl.
*C12N 9/04* (2006.01)
*C12N 9/06* (2006.01)
*C07H 21/04* (2006.01)

(52) U.S. Cl. .................. 435/190; 435/191; 435/252.3; 435/320.1; 536/23.2

(58) Field of Classification Search ................. 435/190, 435/191, 252.3, 320.1; 536/23.2
See application file for complete search history.

(56) References Cited

FOREIGN PATENT DOCUMENTS

JP          61-268178        11/1986
JP          11-155579        6/1999

OTHER PUBLICATIONS

Sequence search alignment between Applicant's Seq Id No.: 2 and Accession No. Q8RIU8.*
T. Horiuchi, et al., Agric. Biol. Chem., vol. 53, No. 1, XP-002022262, pp. 103-110, "Purification and Properties of Fructosyl-Amino Acid Oxidase from Corynebacterium SP. 2-4-1", 1989.
Z. Lin, et al., Biotechnol. Prog., vol. 15, No. 3, XP-000892792, pp. 467-471, "Functional Expression of Horseradish Peroxidase in E. coli by Directed Evolution", May 1999.
R. Sakaue, et al., Applied and Environmental Microbiology, vol. 69, No. 1, XP-002286929, pp. 139-145, "Thermostabilization of Bacterial Fructosyl-Amino Acid Oxidase by Directed Evolution", Jan. 2003.

* cited by examiner

*Primary Examiner*—Tekchand Saidha
(74) *Attorney, Agent, or Firm*—Oblon, Spivak, McClelland, Maier & Neustadt, P.C.

(57) ABSTRACT

The present invention provides a novel fructosyl amino acid oxidase that is excellent in thermal stability. Moreover, the present invention provides a fructosyl amino acid oxidase gene encoding the novel fructosyl amino acid oxidase, a recombinant DNA in which the gene is inserted into a vector DNA, a transformant or transductant containing this gene, and a process for producing the novel fructosyl amino acid oxidase, which comprises culturing the transformant or transductant in a medium and collecting the novel fructosyl amino acid oxidase from the culture product.

4 Claims, 4 Drawing Sheets

Fig. 1

Fig. 2 buffer solution : 0.1 M phosphate buffer , pH 8.0

Fig. 3

Fig. 4 treatment : 0.1 M phosphate buffer , pH 8.0, 10 min

SEQUENCE LISTING

<160> NUMBER OF SEQ ID NOS: 14

<210> SEQ ID NO 1
<211> LENGTH: 372
<212> TYPE: PRT
<213> ORGANISM: Corynebacterium sp.

<400> SEQUENCE: 1

Met Ser Ser Thr Ala Thr Lys His Val Ala Val Ile Gly Gly Gly Ile
1               5                   10                  15

Leu Gly Val Ser Thr Ala Val His Leu Leu Arg Gln Gly Ala Thr Val
                20                  25                  30

Thr Leu Leu Thr Glu Gln Gly Leu Ala Ser Glu Ala Thr Gly Arg Ser
            35                  40                  45

Leu Ser Trp Leu Asn Ser Ala Gly Glu Arg Ser Thr Pro Tyr His Gln
        50                  55                  60

Leu Arg Ile Ala Gly Val Asp Arg Tyr Arg Thr Leu Phe Ala Ala Asp
65                  70                  75                  80

Pro Ser Arg Glu Trp Leu Gln Phe Gly Gly Gly Leu Met Trp Asn Ala
                85                  90                  95

Ala Gly Glu Ser Glu Val Thr Lys Ala Arg His Ala Tyr Glu Lys Ser
                100                 105                 110

Ile Gly Tyr Asp Ser Gln Leu Leu Ala Pro Glu Glu Ile Gly Ser Val
            115                 120                 125

Thr Pro Gly Ile Asp Ala Ser Ala Val Pro Glu Asn Ala Ile Phe Asn
        130                 135                 140

Pro Gly Glu Gly Trp Val Ser Leu Pro Asp Leu Val Asn Phe Leu Met
145                 150                 155                 160

Glu Glu Phe His Ala Leu Gly Gly Gln Leu Val Leu Asn Ala Gly Lys

```
                   165                 170                 175
Ala Ser Val Met Val Glu Gly Gly Arg Ala Thr Ala Val Glu Thr Ala
                180                 185                 190

Thr Gly Glu Thr Tyr Pro Ala Asp Ala Val Leu Val Ala Cys Gly Ala
            195                 200                 205

Ala Thr Pro Ala Val Val Lys Pro Leu Gly Val Glu Ile Pro Asn Gly
        210                 215                 220

Ser Pro Val Ser Met Leu Val Val Thr Lys Pro Val Glu His Gln Val
225                 230                 235                 240

Ala Ala Val Met Asn Thr Pro Arg Ala Ala Val Arg Pro Asn Pro Gly
                245                 250                 255

Asn Thr Phe Ala Leu Asp His Asp Trp Tyr Glu Gly His Ile Thr Glu
            260                 265                 270

His Ala Asp Gly Ser Phe Thr Ile Pro Asp Asp Val Val Gln Glu Leu
        275                 280                 285

Ala Asp Glu Ser Ser Lys Leu Ile Ala Gly Asn Pro Glu Leu Lys Pro
290                 295                 300

Ala Ser Trp Lys Ile Gly Tyr Lys Pro Ile Pro Gly Asp Gly Glu Pro
305                 310                 315                 320

Val Phe Gly Glu Leu Gly Arg Val Pro Gly Cys Phe Val Ala Phe Thr
                325                 330                 335

His Ser Gly Ala Thr Leu Gly Leu Ile Ala Gly Glu Leu Leu Ser Gly
            340                 345                 350

Glu Ile Leu Thr Gly Asp Lys His Pro Met Phe Ala Thr Phe Arg Pro
        355                 360                 365

Gly Arg Phe Ser
    370

<210> SEQ ID NO 2
<211> LENGTH: 372
<212> TYPE: PRT
<213> ORGANISM: Corynebacterium sp.

<400> SEQUENCE: 2

Met Ser Ser Thr Ala Thr Lys His Val Ala Val Ile Gly Gly Gly Ile
1               5                   10                  15

Leu Gly Val Ser Thr Ala Val His Leu Leu Arg Gln Gly Ala Thr Val
                20                  25                  30

Thr Leu Leu Thr Glu Gln Gly Leu Ala Ser Glu Ala Thr Gly Arg Ser
            35                  40                  45

Leu Ser Trp Leu Asn Ser Ala Gly Glu Arg Ser Ala Pro Tyr His Gln
        50                  55                  60

Leu Arg Ile Ala Gly Val Asp Arg Tyr Arg Thr Leu Phe Ala Ala Asp
65                  70                  75                  80

Pro Ser Arg Glu Trp Leu Gln Phe Gly Gly Leu Met Trp Asn Ala
                85                  90                  95

Ala Gly Glu Ser Glu Val Thr Lys Ala Arg His Ala Tyr Glu Lys Ser
                100                 105                 110

Ile Gly Tyr Asp Ser Gln Leu Leu Ala Pro Glu Glu Ile Gly Ser Val
            115                 120                 125

Thr Pro Gly Ile Asp Ala Ser Ala Val Pro Glu Asn Ala Ile Phe Asn
        130                 135                 140

Pro Gly Glu Gly Trp Val Ser Leu Pro Asp Leu Val Asn Phe Leu Met
145                 150                 155                 160
```

```
Glu Glu Phe His Ala Leu Gly Gly Gln Leu Val Leu Asn Ala Gly Lys
            165                 170                 175

Ala Ser Val Met Val Glu Gly Gly Arg Ala Thr Gly Val Glu Thr Ala
            180                 185                 190

Thr Gly Glu Thr Tyr Pro Ala Asp Ala Val Leu Val Ala Cys Gly Ala
            195                 200                 205

Ala Thr Pro Ala Val Val Lys Pro Leu Gly Val Glu Ile Pro Asn Gly
            210                 215                 220

Ser Pro Val Ser Met Leu Val Thr Lys Pro Val Glu His Gln Val
225                 230                 235                 240

Ala Ala Val Leu Asn Thr Pro Arg Ala Ala Val Arg Pro Asn Pro Gly
            245                 250                 255

Ser Thr Phe Ala Met Asp His Asp Trp Tyr Glu Gly His Ile Thr Glu
            260                 265                 270

His Ala Asp Gly Ser Phe Thr Ile Pro Asp Asp Val Val Gln Glu Leu
            275                 280                 285

Ala Asp Glu Ser Ser Lys Leu Ile Ala Gly Asn Pro Glu Leu Lys Pro
            290                 295                 300

Ala Ser Trp Lys Ile Gly Tyr Lys Pro Ile Pro Gly Asp Gly Glu Pro
305                 310                 315                 320

Val Phe Gly Glu Leu Gly Arg Val Pro Gly Cys Phe Val Ala Phe Thr
            325                 330                 335

His Ser Gly Ala Thr Leu Gly Leu Ile Ala Gly Glu Leu Leu Ser Gly
            340                 345                 350

Glu Ile Leu Thr Gly Asp Lys His Pro Met Phe Ala Thr Phe Arg Pro
            355                 360                 365

Gly Arg Phe Ser
    370

<210> SEQ ID NO 3
<211> LENGTH: 1116
<212> TYPE: DNA
<213> ORGANISM: Corynebacterium sp.

<400> SEQUENCE: 3
atgtcctcca ccgctaccaa gcatgtcgcc gtcattggcg gcggcatcct gggcgtctcc      60
accgccgtcc acctgctccg ccaaggcgca acagtcaccc tcttgaccga acagggcctc     120
gccagcgaag ccacgggccg gtccttgtcc tggctcaact ccgccgggga acgctccact     180
ccctatcacc agctgcgcat cgctggcgtt gaccggtacc gcacgctgtt cgccgccgat     240
cccagccggg aatggttgca gttcgggggc gggctcatgt ggaacgccgc cggggaaagt     300
gaggtcacca agcccggca cgcctacgag aagtccatcg gctacgactc ccaactgctg     360
gcccctgaag aaatcggctc ggtcacgcca ggcatcgacg ccagtgccgt cccggagaac     420
gcaatcttca tcctggcga gggctgggtc agcctgccgg acctggtgaa cttcctgatg     480
gaggaattcc acgccctggg cggccagttg gtcctcaacg caggtaaagc ctcggtgatg     540
gtcgagggcg gccgggctac cgcggtcgaa accgccaccg tgaaaccta ccccgcggac     600 gccgttctcg tagcctgcgg tgccgcgacg ccggccgtcg taaaaccgct cggggtcgag     660
ataccgaacg gttccccggt ctccatgctg gttgttacca agcccgtgga gcaccaggtc     720
gcggcagtga tgaatacgcc gcgcgctgcc gtgcgaccca atccgggtaa cacttttgcc     780
ttggatcacg actggtatga agggcacatc actgagcacg cggacggttc gttcaccatc     840
ccggatgatg tcgtccagga attggcagac gagtcatcca agctgatcgc aggaaacccc     900
```

```
gagctcaagc cggcatcgtg gaagatcggt tacaagccga tcccgggcga cggcgaacca    960
gtcttcgggg aactcggccg agtaccgggc tgcttcgtgg ctttcaccca ctcaggtgcc   1020
accctgggcc tcatcgcagg cgaattgctc tccggggaga tcctgacggg ggacaagcac   1080
cccatgttcg ccacgttccg gccgggccgg ttctcc                             1116

<210> SEQ ID NO 4
<211> LENGTH: 1116
<212> TYPE: DNA
<213> ORGANISM: Artificial Sequence
<220> FEATURE:
<223> OTHER INFORMATION: Synthetic DNA

<400> SEQUENCE: 4
atgagcagca ctgctaccaa acatgtggcg gttattggtg aggtattct ggtgttagc      60 actgcggttc atctgctgcg tcaaggtgca actgttaccc tgctgaccga acagggtctg   120
gcgagcgaag cgaccggtat atccctgtcc tggctcaact ccgccgggga acgctccgct   180
ccctatcacc agctgcgcat cgctggcgtt gaccggtacc gcacgctgtt cgccgccgat   240
cccagccggg aatggttgca gttcggggc gggctcatgt ggaacgccgc cggggaaagt    300
gaggtcacca agcccggca cgcctacgag aagtccatcg gctacgactc ccaactgctg    360
gcccctgaag aaatcggctc ggtcacgcca ggcatcgacg ccagtgccgt cccggagaac   420
gcaatcttca atcctggcga gggctgggtc agcctgccgg acctggtgaa cttcctgatg   480
gaggaattcc acgccctggg cggccagttg gtcctcaacg caggtaaagc ctcggtgatg   540
gtcgagggcg gccgggctac cggcgtcgaa accgccaccg gtgaaaccta ccccgcggac   600
gccgttctcg tagcctgcgg tgccgcgacg ccggccgtca taaaccgct cggggtcgag    660 ataccgaacg gttccccggt ctccatgctg gttgttacca gcccgtggga gcaccaggtc   720
gcggcagtgc tgaatacgcc gcgcgctgcc gtgcgaccca atccgggtag cacttttgcc   780
atggatcacg actggtatga agggcacatc actgagcacg cggacggttc gttcaccatc   840
ccggatgatg tcgtccagga attggcagac gagtcatcca gctgatcgc aggaaacccc    900 gagctcaagc cggcatcgtg gaagatcggt tacaagccga tcccgggcga cggcgaacca   960
gtcttcgggg aactcggccg agtaccgggc tgcttcgtgg ctttcaccca ctcaggtgcc   1020
accctgggcc tcatcgcagg cgaattgctc tccggggaga tcctgacggg ggacaagcac   1080
cccatgttcg ccacgttccg gccgggccgg ttctcc                             1116

<210> SEQ ID NO 5
<211> LENGTH: 24
<212> TYPE: DNA
<213> ORGANISM: Artificial Sequence
<220> FEATURE:
<223> OTHER INFORMATION: Synthetic DNA

<400> SEQUENCE: 5
tatgagcagc actgctacca aaca                                            24

<210> SEQ ID NO 6
<211> LENGTH: 38
<212> TYPE: DNA
<213> ORGANISM: Artificial Sequence
<220> FEATURE:
<223> OTHER INFORMATION: Synthetic DNA

<400> SEQUENCE: 6
```

-continued tgtggcggtt attggtggag gtattctggg tgttagca                38

<210> SEQ ID NO 7
<211> LENGTH: 42
<212> TYPE: DNA
<213> ORGANISM: Artificial Sequence
<220> FEATURE:
<223> OTHER INFORMATION: Synthetic DNA

<400> SEQUENCE: 7
ctgcggttca tctgctgcgt caaggtgcaa ctgttaccct gc           42

<210> SEQ ID NO 8
<211> LENGTH: 36
<212> TYPE: DNA
<213> ORGANISM: Artificial Sequence
<220> FEATURE:
<223> OTHER INFORMATION: Synthetic DNA

<400> SEQUENCE: 8
tgaccgaaca gggtctggcg agcgaagcga ccggta                  36

<210> SEQ ID NO 9
<211> LENGTH: 38
<212> TYPE: DNA
<213> ORGANISM: Artificial Sequence
<220> FEATURE:
<223> OTHER INFORMATION: Synthetic DNA

<400> SEQUENCE: 9
accaataacc gccacatgtt tggtagcagt gctgctca                38

<210> SEQ ID NO 10
<211> LENGTH: 40
<212> TYPE: DNA
<213> ORGANISM: Artificial Sequence
<220> FEATURE:
<223> OTHER INFORMATION: Synthetic DNA

<400> SEQUENCE: 10
gcagcagatg aaccgcagtg ctaacaccca gaataccacc             40

<210> SEQ ID NO 11
<211> LENGTH: 39
<212> TYPE: DNA
<213> ORGANISM: Artificial Sequence
<220> FEATURE:
<223> OTHER INFORMATION: Synthetic DNA

<400> SEQUENCE: 11
gaccctgttc ggtcagcagg gtaacagttg caccttgac              39

<210> SEQ ID NO 12
<211> LENGTH: 25
<212> TYPE: DNA
<213> ORGANISM: Artificial Sequence
<220> FEATURE:
<223> OTHER INFORMATION: Synthetic DNA

<400> SEQUENCE: 12
gatctaccgg tcgcttcgct cgcca                             25

<210> SEQ ID NO 13
<211> LENGTH: 39
<212> TYPE: DNA
<213> ORGANISM: Artificial Sequence

```
<220> FEATURE:
<223> OTHER INFORMATION: Synthetic DNA

<400> SEQUENCE: 13
gaagccacgg gcggatccct gtcctggctc aactccgcc                    39

<210> SEQ ID NO 14
<211> LENGTH: 38
<212> TYPE: DNA
<213> ORGANISM: Artificial Sequence
<220> FEATURE:
<223> OTHER INFORMATION: Synthetic DNA

<400> SEQUENCE: 14
gggaattcca tatgctagga gaaccggccc ggccggaa                     38
```

FRUCTOSYL AMINO ACID OXIDASE

FIELD OF THE INVENTION

The present invention relates to a novel fructosyl amino acid oxidase having stability under high temperatures, a gene encoding the novel fructosyl amino acid oxidase, and a process for producing the oxidase.

BACKGROUND OF THE INVENTION

A fructosyl amino acid oxidase catalyzes an action to generate glyoxylic acid or α-ketoaldehyde, α-amino acid and hydrogen peroxide by oxidizing iminodiacetic acid or a derivative thereof (also referred to as the "Amadori compound") in the presence of oxygen. The fructosyl amino acid oxidase was discovered in fungi and bacteria. Analytical methods using these enzymes for measuring the Amadori compound included in foods and generated in vivo have been proposed (JP Patent Publication (Kokoku) No. 5-33997, JP Patent Publication (Kokoku) No. 6-65300, JP Patent Publication (Kokai) No. 2-195900, JP Patent Publication (Kokai) No. 3-155780, JP Patent Publication (Kokai) No. 4-4874, JP Patent Publication (Kokai) No. 5-192193, and JP Patent Publication (Kokai) No. 6-4686).

Recently in the field of clinical diagnosis, HbA1c (glycosylated hemoglobin) has attracted attention as a blood glucose control marker, which is important in diagnosing the pathological conditions and controlling the symptoms of diabetic patients. As a method for rapidly and simply measuring HbA1c, an enzymatic measurement method using fructosyl amino acid oxidase has been proposed and practically applied. Specifically, this method involves degrading HbA1c with protease or the like, and then measuring the thus-freed fructosyl valine (a derivative of iminodiacetic acid wherein α-amino group of valine is glycosylated). Among various fructosyl amino acid oxidases that are used as enzymes in this measurement method, an enzyme having high activity for fructosyl valine, which is a substrate, but having no activity for ε-fructosyl lysine (a type of Amadori compound wherein ε-amino group of lysine is glycosylated) is particularly excellent in terms of its rapidity and accuracy of measurement. An example of such an enzyme is fructosyl amino acid oxidase derived from bacteria of the genus *Corynebacterium*. However, the above fructosyl amino acid oxidase is deactivated 90% or more by heat treatment at 45° C. for 10 minutes. Because of this low heat resistance, the fructosyl amino acid oxidase has a problem in its storage stability when it is prescribed in a kit reagent as an enzyme for clinical diagnosis.

SUMMARY OF THE INVENTION

Objects of the present invention are to overcome such defects of the conventional fructosyl amino acid oxidase, and thus to provide a fructosyl amino acid oxidase having high stability in a high temperature range, a gene encoding the oxidase, and a process for producing the oxidase.

Through intensive studies directed toward the above objects, we have completed the present invention by finding, for example, that a novel fructosyl amino acid oxidase showing high stability in a high temperature range can be obtained by modifying a fructosyl amino acid oxidase gene derived from *Corynebacterium* (JP Patent Publication (Kokai) No. 11-155579).

That is, the present invention is a novel fructosyl amino acid oxidase having the following physicochemical properties of:

(a) action and substrate specificity: catalyzing reaction to generate glyoxylic acid or α-ketoaldehyde, α-amino acid and hydrogen peroxide by oxidizing iminodiacetic acid or a derivative thereof in the presence of oxygen, but not acting on ε-fructosyl lysine;
(b) optimum pH range: 7.5 to 8.5;
(c) stable pH range: 5.0 to 10.0;
(d) optimum temperature range for action: 40° C. to 50° C.;
(e) thermal stability: showing 80% or more remaining activity when heat treatment is performed for 10 minutes at 50° C.; and
(f) molecular weight: approximately 88,000 (determined by gel filtration), approximately 44,000 (determined by SDS-PAGE).

Further, the present invention is the following protein (a), (b) or (c) having a novel fructosyl amino acid oxidase activity:

(a) a protein comprising an amino acid sequence represented by SEQ ID NO: 2;
(b) a protein comprising an amino acid sequence derived from the amino acid sequence represented by SEQ ID NO: 2 by deletion, substitution and/or addition of one or several amino acids, and having a novel fructosyl amino acid oxidase activity; or
(c) a protein comprising an amino acid sequence showing 80% or more homology with the amino acid sequence represented by SEQ ID NO: 2, and having a novel fructosyl amino acid oxidase activity.

Further, the present invention is a gene encoding the following protein (a), (b), or (c) having a novel fructosyl amino acid oxidase activity.

(a) a protein comprising the amino acid sequence represented by SEQ ID NO: 2;
(b) a protein comprising an amino acid sequence derived from the amino acid sequence represented by SEQ ID NO: 2 by deletion, substitution and/or addition of one or several amino acids, and having a novel fructosyl amino acid oxidase activity; or
(c) a protein comprising an amino acid sequence showing 80% or more homology with the amino acid sequence represented by SEQ ID NO: 2, and having a novel fructosyl amino acid oxidase activity.

Further, the present invention is a gene encoding the following protein (a), (b), or (c) having a novel fructosyl amino acid oxidase activity:

(a) a DNA comprising a nucleotide sequence represented by SEQ ID NO: 4;
(b) a DNA hybridizing under stringent conditions to a DNA comprising a nucleotide sequence complementary to the entire or a portion of 15 nucleotides or more of the DNA comprising the nucleotide sequence represented by SEQ ID NO: 4, and encoding a protein having a novel fructosyl amino acid oxidase activity; or
(c) a DNA showing 80% or more homology with the entire or a portion of 15 nucleotides or more of the DNA comprising the nucleotide sequence represented by SEQ ID NO: 4, and encoding a protein having a novel fructosyl amino acid oxidase activity.

Further, the present invention is a recombinant DNA wherein the above gene is inserted into a vector DNA.

Further, the present invention is a transformant or a transductant containing the above recombinant DNA.

Further, the present invention is a process for producing a novel fructosyl amino acid oxidase which comprises culturing the above transformant or transductant in a medium, and collecting the novel fructosyl amino acid oxidase from the culture product.

BEST MODE FOR CARRYING OUT THE INVENTION

The present invention is described in detail as follows.

The novel fructosyl amino acid oxidase of the present invention (hereinafter, referred to as "oxidase of the present invention") is a fructosyl amino acid oxidase having the following physicochemical properties:

(a) Action and substrate specificity: The fructosyl amino acid oxidase catalyzes reaction as shown in the following formula to generate glyoxylic acid or α-ketoaldehyde, α-amino acid and hydrogen peroxide by oxidizing iminodiacetic acid or a derivative thereof (Amadori compound) in the presence of oxygen.

In this formula, $R_1$ represents group —OH, —[CH(OH)]$_n$ —CH$_2$OH or —(CH$_2$)$_n$—CH$_3$, n represents an integer from 0 to 4, and $R_2$ represents a side chain residue of α-amino acid. Any enzyme that has the above action and substrate specificity may be used in the present invention, as long as it is used for rapid and simple measurement of HbA1c, which is the blood glucose control marker important in diagnosing diabetes. Such an enzyme is preferably the oxidase of the present invention having high activity for fructosyl valine, and is particularly preferably the oxidase of the present invention which has high activity for fructosyl valine, and does not act or hardly act on ε-fructosyl lysine. Examples of such an enzyme having the above action and substrate specificity include a fructosyl amino acid oxidase derived from bacteria of the genus *Corynebacterium* (JP Patent Publication (Kokoku) No. 6-65300) and the like.

(b) Optimum pH range: 7.5 to 8.5

The optimum pH is found by performing enzyme reaction at 37° C. and at each pH using a buffer solution such as McIlvaine buffer (pH 4.0 to 6.0), 100 mM potassium phosphate buffer (pH 6.0 to 8.5), or 100 mM sodium hydrogen carbonate-sodium carbonate buffer solutions (pH 9.0 to 10.0).

(c) Stable pH range: 5.0 to 10.0

The stable pH range is found by measuring the remaining activity of the enzyme when treatment has been performed at 37° C. for 10 minutes at each pH using a buffer solution such as McIlvaine buffer solution (pH 3.0 to 6.0), 100 mM potassium phosphate buffer solution (pH 6.0 to 8.5), or 100 mM sodium hydrogen carbonate-sodium carbonate buffer solution (pH 9.0 to 10.0).

(d) Optimum temperature range for action: 40° C. to 50° C.

The optimum temperature range for action is found by measuring the activity of the enzyme at various temperatures using reaction solutions in a later-described method for measuring activity.

(e) Thermal stability: 80% or more activity remains after heat treatment at 50° C. for 10 minutes After treatment at 50° C. for 10 minutes using 100 mM potassium phosphate buffer solution (pH 8.0), the remaining activity of the enzyme is measured. The oxidase of the present invention is a novel enzyme differing from conventional enzymes, particularly in that it has high stability in a high temperature range. An example of such an enzyme is the oxidase of the present invention showing 50% or more, preferably 80% or more, and particularly preferably 90% or more remaining activity under the above treatment conditions.

(f) Molecular weight: approximately 88,000 (determined by gel filtration), and approximately 44,000 (determined by SDS-PAGE)

The molecular weights are respectively found by a column gel filtration method using Sephadex G-200 and by the SDS-PAGE method using multi-gel 10/20 (Daiichi Pure Chemicals), according to the standard method.

As described above, the oxidase of the present invention differs from any known fructosyl amino acid oxidase in physicochemical properties, and thus is a novel fructosyl amino acid oxidase. Particularly in that the oxidase has property of not acting on ε-fructosyl lysine and has high thermal stability, it is significantly superior to known enzymes. Therefore, the oxidase can be prescribed in a kit reagent as an enzyme for clinical diagnosis that is excellent in terms of storage stability.

Examples of the oxidase of the present invention include those derived from various organisms obtained by screening nature, and those obtained by modifying conventionally known fructosyl amino acid oxidases. A specific example is the following oxidase of the present invention (a), (b) or (c):

(a) a fructosyl amino acid oxidase containing the amino acid sequence represented by SEQ ID NO: 2;
(b) a fructosyl amino acid oxidase containing an amino acid sequence derived from the amino acid sequence represented by SEQ ID NO: 2 by deletion, substitution and/or addition of one or several amino acids; or
(c) a fructosyl amino acid oxidase containing an amino acid sequence showing 80% or more homology with the amino acid sequence represented by SEQ ID NO: 2.

"Deletion, substitution and/or addition of one or several amino acids" means deletion, substitution and/or addition of any number of amino acids, for example, 1 to 20, preferably 1 to 10, and more preferably 1 to 5.

Further, "showing 80% or more homology" is not specifically limited, as long as homology with the amino acid sequence represented by SEQ ID NO: 2 is 80% or more. Such a homology is, for example, 80% or more, preferably 90% or more, and most preferably 95% or more.

Examples of a fructosyl amino acid oxidase gene (hereinafter referred to as "the gene of the present invention") encoding the novel fructosyl amino acid oxidase of the present invention include a gene encoding the above oxidase of the present invention (a), (b) or (c), and a gene encoding the oxidase of the present invention containing the following DNA (a), (b), or (c):

(a) a DNA comprising the nucleotide sequence represented by SEQ ID NO: 4;
(b) a DNA hybridizing under stringent conditions to a DNA comprising a nucleotide sequence complementary to the entire or a portion of 15 nucleotides or more of the DNA comprising the nucleotide sequence represented by SEQ ID NO: 4, and encoding a protein having novel fructosyl amino acid oxidase activity; or
(c) a DNA showing 80% or more homology with the entire or a portion of 15 nucleotides or more of the DNA comprising the nucleotide sequence represented by SEQ ID NO: 4, and encoding a protein having a novel fructosyl amino acid oxidase activity.

Here, "a DNA hybridizing under stringent conditions" means DNA obtained by a method using DNA as a probe, such as colony hybridization, plaque hybridization or southern blot hybridization. Specific examples of such DNA include DNA that can be identified by performing hybridization at 65° C. using a filter to which DNA derived from colonies or plaques, or fragments of the DNA have been immobilized, washing the filter under a condition of 65° C. Hybridization can be performed according to the method described in Current Protocols in Molecular Biology (WILEY Interscience, 1989) or the like. An example of DNA hybridizing under stringent conditions is a DNA having a certain percentage or greater homology with the nucleotide sequence of DNA to be used as a probe. In the present invention, homology of "DNA containing a nucleotide sequence showing 80% or more homology with the entire or a portion of 15 nucleotides or more of a nucleotide sequence" is, for example, 80% or more, preferably 90% or more, and most preferably 95% or more.

Next, methods for obtaining the oxidase of the present invention and the gene of the present invention are described.

The oxidase of the present invention can be obtained from nature by searching enzymes originating from microorganisms, animals, or plants. The oxidase of the present invention can also be obtained by modifying fructosyl amino acid oxidase (hereinafter referred to as "oxidase having different properties") having physicochemical properties different from the enzyme of the present invention using a method such as genetic engineering techniques or mutation treatment. An oxidase having properties different from the present invention is, for example, the above-mentioned known oxidase, or the like. It may also be a new fructosyl amino acid oxidase obtained by a search, a fructosyl amino acid oxidase obtained by modification using genetic engineering techniques, or the like. An example of the known oxidase is preferably a fructosyl amino acid oxidase derived from bacteria of the genus *Corynebacterium* (JP Patent Publication (Kokoku) No. 6-65300).

An example of a method for modifying physicochemical properties of oxidase having different properties involves:
irradiating microorganisms or the like producing the oxidase with, for example, ultraviolet rays, X-rays, or radioactive rays; or
allowing the microorganisms to contact with an agent for mutagenesis such as ethylmethane sulfonate, N-methyl-N'-nitro-N-nitrosoguanidine, or nitrous acid;
obtaining microorganisms producing the modified oxidase of the present invention; and then
obtaining the oxidase of the present invention from the obtained microorganisms.

However, in general, the oxidase of the present invention can be obtained by modifying a gene encoding oxidase or the like having different properties using genetic engineering techniques. As a gene encoding the oxidase having different properties to be used in the present invention, any gene encoding any fructosyl amino acid oxidase can be used, as long as it is a gene with which the oxidase of the present invention can be obtained by modification.

A gene encoding the oxidase having different properties to be used in the present invention is obtained by a normally and generally employed method for cloning a gene. For example, chromosome DNA or mRNA is extracted from microbial bodies and various cells capable of producing oxidase having different properties by a standard method, such as a method described in Current Protocols in Molecular Biology (WILEY Interscience, 1989). Further, cDNA can be synthesized using mRNA as a template. A library of the thus-obtained chromosome DNA or cDNA is constructed. Next, an appropriate probe DNA is synthesized based on the amino acid sequence of the above oxidase having different properties, followed by screening of the chromosome DNA or cDNA library using the probe; or appropriate primer DNAs are prepared based on the above amino acid sequence, DNA containing a target gene fragment is amplified by an appropriate polymerase chain reaction (PCR method) such as 5' RACE or 3'RACE method, followed by a ligation of them, so that a DNA containing the full-length target gene can be obtained. A preferred example of the thus-obtained gene encoding the oxidase having different properties is a fructosyl amino acid oxidase gene derived from bacteria of the genus *Corynebacterium* (JP Patent Publication (Kokai) No. 11-155579). In terms of handling, these genes are preferably ligated to various vectors according to standard methods. For example, the gene can be obtained by extraction and purification using, for example, QIAGEN (Qiagen), from a recombinant plasmid pFA5 DNA (JP Patent Publication (Kokai)) containing a gene, which encodes oxidase having different properties and is derived from an isolated *Corynebacterium* sp. Strain 2.4.1. In addition, examples of a vector DNA that can be used in the present invention include plasmid vector DNA's such a pUC 119 (Takara Shuzo), pBR322 (Takara Shuzo), and pMAL-C2 (NEW England Labs), and bacteriophage vector DNA's, such as λEMBL3 (Stratagene), and λDASH II (FUNAKO-SHI). Specifically, for example, pBluescript II SK+ (Stratagene) is preferred.

Next, the oxidase of the present invention can be obtained by modifying a gene encoding the oxidase having different properties obtained by the above method. Specifically, in the present invention, modification of the gene encoding the oxidase having different properties results in modification of an amino acid sequence of the oxidase having different properties to be translated by the gene. Thus, in addition to the oxidase of the present invention, an unmodified oxidase having different properties and various fructosyl amino acid oxidases having different physicochemical properties can be obtained.

A gene that is used for modification and encodes oxidase having different properties is not specifically limited. An embodiment of the present invention is a gene encoding oxidase having different properties derived from *Corynebacterium* sp. strain 2.4.1 (JP Patent Publication (Kokai) No. 11-155579, SEQ ID NO: 3). Further, another embodiment is a gene having a nucleotide sequence that is modified so as not to have or to have addition, deletion, or substitution of amino acid residues appropriate for expression of the gene in a host organism.

As a method for modifying the above gene, any known method can be used. Examples of such a method include one that allows the above recombinant plasmid pFA5 DNA (JP Patent Publication (Kokai) No. 11-155579) to contact a chemical agent for mutation such as hydroxyl amine, or nitrous acid, or a point mutation method such as one that involves random modification using the PCR method, a known technique, the site-directed mutagenesis method for causing a site-directed substitution or a deletion mutation using a commercial kit, and an oligo nucleotide mutagenesis method, which selectively cleaves the recombinant plasmid DNA, and removes or adds and ligates the selected oligonucleotide. Subsequent to the above treatment, the recombinant DNAs are purified by a QIAGEN desalting column (Qiagen) or the like, thereby obtaining various recombinant DNAs.

For example, *Escherichia coli* K12, preferably *Escherichia coli* JM109 or DH5α (both produced by TOYOBO), or XL1-Blue (FUNAKOSHI) is transformed or transduced with the various thus-obtained recombinant DNAs, so that transformants or tranductants containing recombinant DNAs having various modified fructosyl amino acid oxidase gene fragments can be obtained. In the case of transformants, for example, a transformant (strain producing the oxidase of the present invention) having target physicochemical properties of the present invention (having stability in a high temperature range) is selected from the obtained transformants (containing a recombinant plasmid DNA that contains various mutant fructosyl amino acid oxidase genes therein).

Next, to select a strain producing the oxidase of the present invention, for example, the following method can be used. First, several replicas are taken using a sterilized velvet cloth or the like from LB agar media on which the above obtained transformants have formed colonies, and are then transferred onto new agar media for culturing. When the replica-plated colonies on the agar media reach a sufficient size, membranes immersed in a lytic agent such as lisozyme are laid on the media. Then, the media are allowed to stand at 37° C. for 1 hour for lysis. At this time, crude enzyme solutions following lysis are adsorbed to the membranes. After the membranes having the crude enzyme solutions adsorbed thereto are allowed to stand at 55° C. for 1 hour, the membrane is laid on a membrane immersed in 0.1 M potassium phosphate buffer solution (pH 8.0) containing fructosyl glycine that is a substrate, peroxidase, TOOS, and 4-amino antipyrine, and then the degree of violet color development is observed. The color development test is also conducted by similar processes for a strain producing an unmodified oxidase having different properties. Thus, a target transformant is selected by comparing color development.

Transformants capable of producing the oxidase of the present invention can be obtained in this manner. An example is the oxidase of the present invention containing the amino acid sequence represented by SEQ ID NO: 2 that is obtained using the above modification method for fructosyl amino acid oxidase (JP Patent Publication (Kokoku) No. 6-65300) derived from bacteria of the genus *Corynebacterium* having the amino acid sequence of SEQ ID NO: 1. If necessary, the gene of the present invention is further repeatedly modified by the above modification method using the transformant capable of producing the oxidase of the present invention, so that the modified oxidase of the present invention having high heat resistance and a transformant capable of producing the oxidase can also be obtained. Specifically, in the present invention, the oxidase of the present invention also includes, for example, a fructosyl amino acid oxidase, which contains an amino acid sequence derived from the amino acid sequence represented by SEQ ID NO: 2 by deletion, substitution and/or addition of one or several amino acids, and a fructosyl amino acid oxidase, which contains an amino acid sequence showing 80% or more homology with the amino acid sequence represented by SEQ ID NO: 2. A specific example is the oxidase (Type 3) of the present invention that is described later in Examples. Type 3 oxidase has an amino acid sequence derived from the amino acid sequence represented by SEQ ID NO: 2 by substitution of an amino acid residue, and has 90% or more homology. Further, an example of the thus-obtained transformant producing the oxidase of the present invention is *Escherichia coli* (*E. coli*) DH5α (pFAH5) producing the oxidase (Type 4) of the present invention, which achieves a remaining activity rate of 90% when heat treatment is performed at 50° C. for 10 minutes and contains the amino acid sequence represented by SEQ ID NO: 2.

Further, an example of the gene of the present invention is a gene (SEQ ID NO: 4) of the above oxidase (Type 4) of the present invention. A plasmid pFAH5, which contains a gene containing SEQ ID NO: 4 encoding SEQ ID NO: 2, was deposited (original deposit date: Nov. 22, 2000) under Accession No. FERM BP-7378 at the International Patent Organism Depositary (IPOD), National Institute of Advanced Industrial Science and Technology, Japan (Central 6, 1-1-1, Higashi, Tsukuba, Ibaraki, Japan), as described above. A further example of the gene of the present invention is one that encodes the oxidase of the present invention, such as a fructosyl amino acid oxidase containing an amino acid sequence derived from the amino acid sequence represented by SEQ ID NO: 2, by deletion, substitution and/or addition of one or several amino acids, and a fructosyl amino acid oxidase containing an amino acid sequence showing 80% or more homology with the amino acid sequence represented by SEQ ID NO: 2. Another example of the gene of the present invention is one that comprises a DNA hybridizing under stringent conditions to a DNA comprising a nucleotide sequence complementary to the entire or a portion of 15 nucleotides or more of a DNA comprising the nucleotide sequence represented by SEQ ID NO: 4, and encoding a protein having the oxidase activity of the present invention, or comprises a DNA showing 80% or more homology with the entire or a portion of 15 nucleotides or more of a DNA comprising the nucleotide sequence represented by SEQ ID NO: 4, and encoding a protein having the oxidase activity of the present invention. Specific examples of "a portion of 15 nucleotides or more" include nucleotide sequences of SEQ ID NOS: 5 to 14, which are partial sequences of SEQ ID NO: 4. Further, another example of a DNA containing a nucleotide sequence showing 80% or more homology is a DNA that comprises a nucleotide sequence derived from that of SEQ ID NO: 4 by substitution of a nucleotide sequence located upstream from the 151$^{st}$ nucleotide with a nucleotide sequence located upstream from the 151$^{st}$ nucleotide of SEQ ID NO: 3, since it encodes the amino acid sequence of SEQ ID NO: 2.

Next, the oxidase of the present invention is produced by culturing microorganisms that are capable of producing the oxidase of the present invention in media, and collecting the fructosyl amino acid oxidase from the culture product. Any microorganism can be used for producing the oxidase of the present invention, as long as it is capable of producing the oxidase of the present invention. Examples of such a microorganism include a transformant or transductant that is obtained as described above and is capable of producing the oxidase of the present invention. For example, the oxidase of the present invention can be produced using a transformant strain, which is capable of producing the oxidase of the present invention and preferably belongs to the genus *Escherichia*. The above microorganism may be cultured using a solid culture method, and is preferably cultured using a liquid culture method. Further, a medium used for culturing the above microorganisms contains, for example, one or more types of nitrogen source, such as yeast extract, peptone, meat extract, corn steep liquor, or exudate of soy bean or wheat koji, which is supplemented with one or more types of inorganic salts, such as potassium dihydrogen phosphate, dipotassium hydrogen phosphate, magnesium sulfate, ferric chloride, ferric sulfate or manganese sulfate. If necessary, the medium may further be supplemented appropriately with a sugar material, vitamin or the like. In addition, it is appropriate to adjust the initial pH for the medium to between 7 and 9. Further, culturing is preferably performed by submerged culture with aeration and agitation, shake culture, static culture, or the like at 30 to 42° C., and preferably at around 37° C. for 6 to 24 hours. To collect the oxidase of the present invention from the culture product after culturing, a general measure for collecting enzymes can be used. For example, microbial bodies are separated from the culture solution by a procedure such as filtration and centrifugation, and then washed. It is preferable to collect the oxidase of the present invention from the microbial bodies. In this case, microbial bodies can be used intact. Preferably, the oxidase of the present invention is collected from microbial bodies by, for example, a method which disrupts microbial bodies using various disruption measures, such as an ultrasonicator, french press, or a dyno-mill, a method which lyses microbial cell walls using a cell wall lysing enzyme, such as lysozme, or a method which extracts enzyme from microbial bodies using a surfactant such as TritonX-100.

To isolate the oxidase of the present invention from the thus-obtained crude enzyme solution, a method generally used for enzyme purification can be used. For example, an appropriate combination of methods of an ammonium sulfate salting-out, organic solvent precipitation, ion exchange chromatography, gel filtration chromatography, adsorption chromatography, and electrophoresis is preferably performed. In this manner, the oxidase of the present invention can be isolated to a degree such that it shows almost a single band in SDS-PAGE. Moreover, enzyme samples differing in their degrees of purification can also be prepared according to their applications by an appropriate combination of the above purification methods.

Examples of a main method for measuring enzyme activity of the oxidase of the present invention include a method that measures the amount of hydrogen peroxide generated by enzyme reaction, and a method which measures the amount of oxygen that is consumed by enzyme reaction. As an example, a method that measures the amount of hydrogen peroxide is shown below. Hereinafter, unless otherwise specified, fructosyl glycine is used as a substrate for measuring activity of the enzyme of the present invention. One unit (1 U) of enzyme titer is defined as the amount of enzyme that produces 1 μmol of hydrogen peroxide per minute when measurement is performed using fructosyl glycine as a substrate.

A. Preparation of Reagent
(1) Reagent 1: POD-4-AA solution
   1.0 kU of peroxidase (TOYOBO, TYPE III), and 100 mg of 4-amino antipyrine (Tokyo Kasei Kogyo) are dissolved in 0.1 M potassium phosphate buffer solution (pH 8.0) and diluted to 1 liter.
(2) Reagent 2: TOOS solution
   500 mg of TOOS (DOJINDO) is dissolved in ion-exchange water, and diluted to 100 ml.
(3) Reagent 3: Substrate solution (150 mM, and final concentration: 5 mM)
   357 mg of fructosyl glycine is dissolved in ion-exchange water, and diluted to 10 ml. When fructosyl valine or ε-fructosyl lysine is used as a substrate, a solution used in this case is prepared by dissolving 417 mg of fructosyl valine or 462 mg of ε-fructosyl lysine in ion-exchange water, and is diluted to 10 ml.

B. Measurement Method
   An enzyme solution is added and mixed with the solution, and then heated (previous heating) at 37° C. for 5 minutes. Subsequently, 100 μl of reagent 3 is added and mixed well with the solution. Absorbance is measured at 555 nm using a spectral photometer (U-2000A, Hitachi). The value to be measured is a change in absorbance at 555 nm measured per minute during the period 1 to 3 minutes after mixing. In addition, control solution is prepared similarly to the above processes, except that 100 μl of ion-exchange water is added, instead of 100 μl of reagent 3. Then, a graph is prepared to show the relation with the volumes of pigment generated as examined using previously prepared standard solutions of hydrogen peroxide, instead of reagent 3, and using ion-exchange water, instead of an enzyme solution. Using this graph, the amount (micromoles) of hydrogen peroxide that is generated per minute at 37° C. is calculated, and the value is defined as an activity unit in an enzyme solution.

EXAMPLE

The present invention will be described more specifically by the following examples. These examples are not intended to limit the technical scope of the present invention.

(A) Preparation of Recombinant Plasmid

A recombinant plasmid DNA having an oxidase gene that has different properties (a gene having the nucleotide sequence of SEQ ID NO: 3, a gene encoding the amino acid sequence of SEQ ID NO: 1), and a recombinant plasmid DNA having an oxidase gene, wherein a nucleotide sequence of a region encoding an amino terminus of this gene had been modified to be appropriate for codon usage of E. coli in order to increase the expression amount of the gene in E. coli, were respectively prepared. To prepare the below-described oxidase of the present invention, any recombinant plasmid DNA may be used. The use of a recombinant plasmid DNA having a modified oxidase gene is effective in producing the oxidase of the present invention in large quantities.

(1) Preparation of recombinant plasmid pFA5 DNA

E. coli DH5α (pFA5) having the above recombinant plasmid of the oxidase gene (the gene having the nucleotide sequence described in SEQ ID NO: 3) was inoculated into 20 ml of an LB medium (1% Bacto-Trypton, 0.5% yeast extract, and 0.25% NaCl), and then cultured by shaking at 37° C. for 20 hours, thereby obtaining the culture product. The above E. coli DH5α (pFA5) was deposited (original deposit date: Nov. 21, 1997) under Accession No. FERM BP-6182 at the National Institute of Advanced Industrial Science and Technology, International Patent Organism Depositary (Central 6, 1-1-1, Higashi, Tsukuba, Ibaraki, Japan). The culture product was centrifuged at 7000 rpm for 5 minutes to collect bacteria, thereby obtaining bacterial bodies. Then, recombinant plasmid pFA5 DNA was extracted and then purified from the bacterial bodies using the QIAGEN tip-100 (Qiagen), so that 100 μg of recombinant plasmid pFA5 DNA was obtained.

(2) Preparation of recombinant plasmid pFAN5 DNA having a modified nucleotide sequence on the amino terminal side An oligonucleotide, which has the partial sequences of SEQ ID NO: 4 that had been designed based on the sequence information of the nucleotide sequence of the amino terminal of SEQ ID NO: 3 so as to apply for the codon usage of E. coli or the complementary strands thereof, the nucleotide sequences of SEQ ID NOS: 5 to 12; and an oligonucleotide, which has the nucleotide sequences of SEQ ID NOS: 13 and 14 that had been designed to amplify by the PCR method the carboxyl terminus of SEQ ID NO: 3, were obtained by the custom synthesis service of Sawaday Technology. Sequences of SEQ ID NOS: 5 to 12 were respectively phosphorylated using T4 Polynucleotide kinase (Takara Shuzo). Meanwhile, PCR reaction was performed using as a template pFA5 DNA having the nucleotide sequence of SEQ ID NO: 3, SEQ ID NOS: 13 and 14 as primers, and Ex Taq polymerase (Takara Shuzo), thereby preparing a gene fragment encoding the C-terminal side. Further, the fragment was digested with Nde I (Daiichi Pure Chemicals) and Bam HI (Takara Shuzo). Furthermore, after pUTE500k' DNA (described in Journal of Biotechnology 52 (1996) 11–20) was digested with Nde I, dephosphorylation was performed by BAP treatment (the reagent used herein was produced by Takara Shuzo). The proper amounts of the thus-obtained 6 phosphorylated oligonucleotides, pFA5 DNA-derived gene fragment, and pUTE500k' DNA fragment were mixed, followed by ligation using Ligation Kit ver.2 (Takara Shuzo). The thus-obtained plasmid was named pFAF5. Further, the plasmid was digested with Bam HI and Bgl II, inserted into pBluescriptII SK$^+$ that had been treated with BAP after cleaved with Bam HI. The product was named pFAN5. Subsequently, 100 μg of pFAN5 DNA was prepared by the method described in (1).

(B) Preparation of the Oxidase of the Present Invention and a Transformant Strain Capable of Producing the Oxidase of the Present Invention (1) Modification procedure (conferring heat resistance)

Using 20 μg of 100 μg of the above recombinant plasmid pFAN5 DNA, XL1-RED (STRATAGENE) (upon proliferation, it tends to make an error in replication of the plasmid, thus it easily causes modification) was transformed according ot the method of D. M. Morrision (Methods in Enzymology, 68, 326–331, 1979), so that approximately 5000 transformant strains were obtained. To collect plasmid DNA's from all the colonies, QUIAGEN sol I (Quiagen) was inoculated on agar media, the colonies were raked together using a spreader, and then collected using a pipetteman. Later, 100 μg of modified recombinant plasmid pFAN5 DNA was obtained by the normal method of QUIAGEN. E. coli DH5α (TOYOBO) was transformed according to the method of D. M. Morrision (Methods in Enzymology, 68, 326–331, 1979) using 20 μg of pFAN5 DNA, and then approximately 1000 strains of transformants having modified plasmids were obtained.

(2) Selection of strains producing the oxidase of the present invention

First, all of the above-obtained transformants were replica-plated on new agar media using a sterilized velvet cloth, and then cultured overnight at 30° C. Hybond-N$^+$ (Amersham) immersed in 10 mg/ml Lysozyme (Sigma) was laid on the thus-obtained replica colonies while air-bubbles were prevented from entering therebetween, and was then allowed to stand at 37° C. for 30 minutes. Subsequently, Hybond-N$^+$ was removed from the agar medium, and then placed on a new agar medium with its face (to which the crude enzyme solution had been attached) on the front surface, followed by treatment at 55° C. for 1 hour. Meanwhile, Hybond-N$^+$ was immersed in 0.1 M potassium phosphate buffer solution (pH 8.0) containing 2 mM fructosyl glycine, 1 mg/ml peroxidase (TOYOBO), 1 mg/ml 4-amino antipyrine (Tokyo Kasei), and 10 mg/ml TOOS (DOJINDO). The thus prepared Hybond-N+ was laid on the previous Hybond-N+, with its face, which had been laid on the colonies, placed inside, and then allowed to stand at 30° C. Then, strains showing color development at a high level around the colonies were selected.

The 10 thus-selected strains that had developed color were cultured with liquid in 2 ml of LB medium (supplemented with 50 µg of Ampicillin), and then allowed to produce the modified fructosyl amino acid oxidase contained in the plasmid. After culturing, the obtained culture product was disrupted by ultrasonication. 0.5 ml of the crude enzyme extract was treated at 47° C. for 10 minutes, and then centrifuged at 12000 rpm for 5 minutes, thereby collecting the supernatant. Activity was measured for the supernatant and the untreated crude enzyme extract, so that remaining activity ratio (activity in the supernatant/activity in the untreated crude enzyme extract) was calculated. Similarly, culturing, extraction, heat treatment and activity measurement were performed. The remaining activity ratio was compared between the modified oxidase and the unmodified oxidase having different properties. Thus, a modified fructosyl amino acid oxidase (Type 1) having an improved remaining activity ratio of 25% and E. coli producing the oxidase were obtained.

(3) Accumulation of modification

A plasmid DNA was prepared from the strain producing the above-obtained (modified) oxidase (Type 1) according to the method described in (A) (1). Mutation is again introduced according to the method of (1). Then, selection was performed by the method of (2) using the previously obtained (modified) oxidase (Type 1) as a control for comparison. The thus-obtained E. coli produced a further modified fructosyl amino acid oxidase (Type 2) showing improved remaining activity ratio of 70% when heat treatment was performed at 47° C. for 10 minutes.

Procedures similar to those above were repeated using E. coli producing the above further modified oxidase (Type 2). The thus-obtained E. coli produced an oxidase (Type 3) of the present invention showing improved remaining activity of 80% when heat treatment was performed at 50° C. for 10 minutes. Further, procedures similar to those above were repeated using E. coli producing the oxidase (Type 3) of the present invention. The thus-obtained E. coli DH5α (pFAH5) produced the oxidase (Type 4) of the present invention showing improved remaining activity of 90% when heat treatment was performed at 50° C. for 10 minutes. The plasmid pFAH5 encoding the gene of the oxidase (Type 4) of the present invention was deposited under Accession No. FERM BP-7378 at the National Institute of Advanced Industrial Science and Technology, International Patent Organism Depositary.

(4) Identification of site where modification occurred

A plasmid retaining the gene of the modified fructosyl amino acid oxidase was collected, and then the nucleotide sequence was determined using 370A DNA Sequencing System (Applied Biosystems). Based on the nucleotide sequence, modified amino acid residues were identified.

Thus, the gene of the oxidase (Type 4) of the present invention was shown to have the nucleotide sequence represented by SEQ ID NO: 4. Further, the predicted amino acid sequence was derived from the amino acid sequence represented by SEQ ID NO: 1 by substitutions of the $60^{th}$ threonine with alanine, the $188^{th}$ alanine with glycine, the $244^{th}$ methionine with leucine, the $257^{th}$ asparagine with serine, and the $261^{st}$ leucine with methionine, as shown in SEQ ID NO: 2. Similarly, the oxidase (Type 3) of the present invention was shown to be derived from the amino acid sequence represented by SEQ ID NO: 1 by substitutions of the $60^{th}$ threonine with alanine, the $188^{th}$ alanine with glycine, the $244^{th}$ methionine with leucine, and the $261^{st}$ leucine with methionine.

(C) Production of the Oxidase of the Present Invention and its Physicochemical Properties Transformants producing the oxidase (Type 4) of the present invention obtained described above and E. coli DH5α (pFAH5) were inoculated in 10 liters of LB-amp medium, and then cultured by shaking using a jar fermenter under conditions of 1 liter/minute of aeration, and an agitation speed of 600 rpm at 30° C. for 24 hours. 10 liters of the obtained culture solution was centrifuged at 7000 rpm for 10 minutes to collect bacteria, and then the bacteria were suspended in 1 liter of 50 mM potassium phosphate buffer solution (pH 8.0). Subsequently, bacterial bodies were disrupted by an ultrasonic wave and centrifuged at 10000 rpm for 10 minutes to collect the supernatant, thereby preparing a crude enzyme solution. To this 5 kU crude enzyme solution potassium chloride was added, resulting in a final concentration of 0.1M. The solution was adsorbed to 1 liter of DEAE-Sephacel column chromatography equilibrated with 0.1 M potassium chloride-containing 50 mM potassium phosphate buffer solution (pH 8.0), and then washed with 1 liter of the same buffer solution. Subsequently, using 10 liters of each 0.2 M potassium chloride-containing 50 mM potassium phosphate buffer solution (pH 8.0) and 0.4 M potassium chloride-containing 50 mM potassium phosphate buffer solution (pH 8.0), the fraction of enzyme activity was eluted using a gradient. The specific activity of the active fraction was 2.4 U/OD280 nm.

Physicochemical properties of the obtained oxidase (Type 4) of the present invention were as shown below.

(1) Action and substrate specificity

Activity of the oxidase of the present invention was measured by the above-described method for measuring enzyme activity using as a substrate fructosyl glycine, fructosyl valine, and ε-fructosyl lysine. The oxidase of the present invention acted on fructosyl glycine and fructosyl valine, but did not act on ε-fructosyl lysine.

(2) Optimum pH

Figure 1:
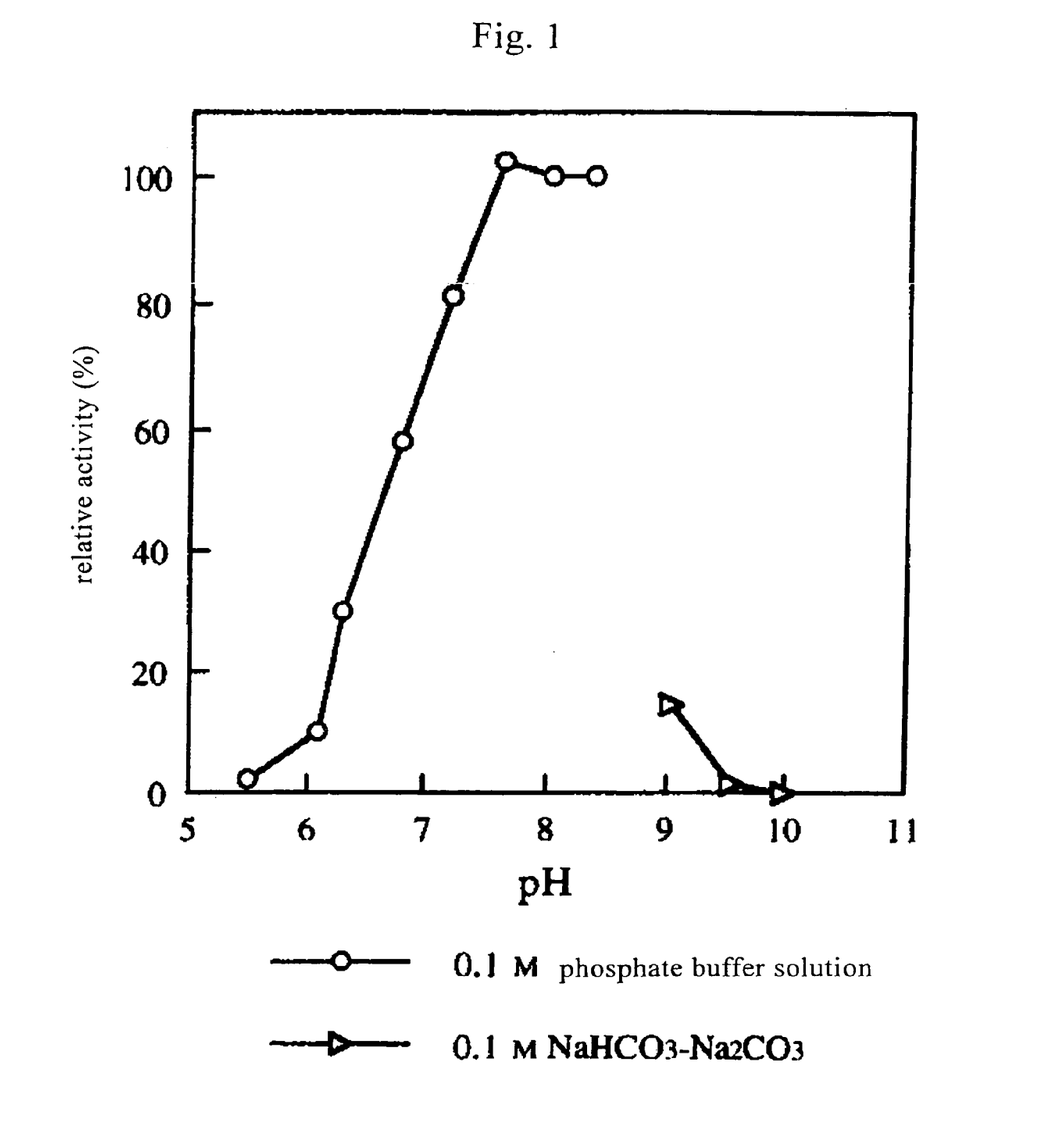
FIG. 1 shows the optimum pH for the oxidase (Type 4) of the present invention.

Enzyme reaction was performed at 37° C. at each pH using as buffer solutions McIlvaine buffer solution (pH 4.0 to 6.0), 100 mM potassium phosphate buffer solution (pH 6.0 to 8.5), and 100 mM sodium hydrogen carbonate-sodium carbonate buffer solution (pH 9.0 to 10.0). The resulting relative activities were as shown in FIG. 1. As shown in FIG. 1, the optimum pH of the oxidase of the present invention ranged from 7.5 to 8.5.

(3) Optimum temperature range for action

Figure 2:
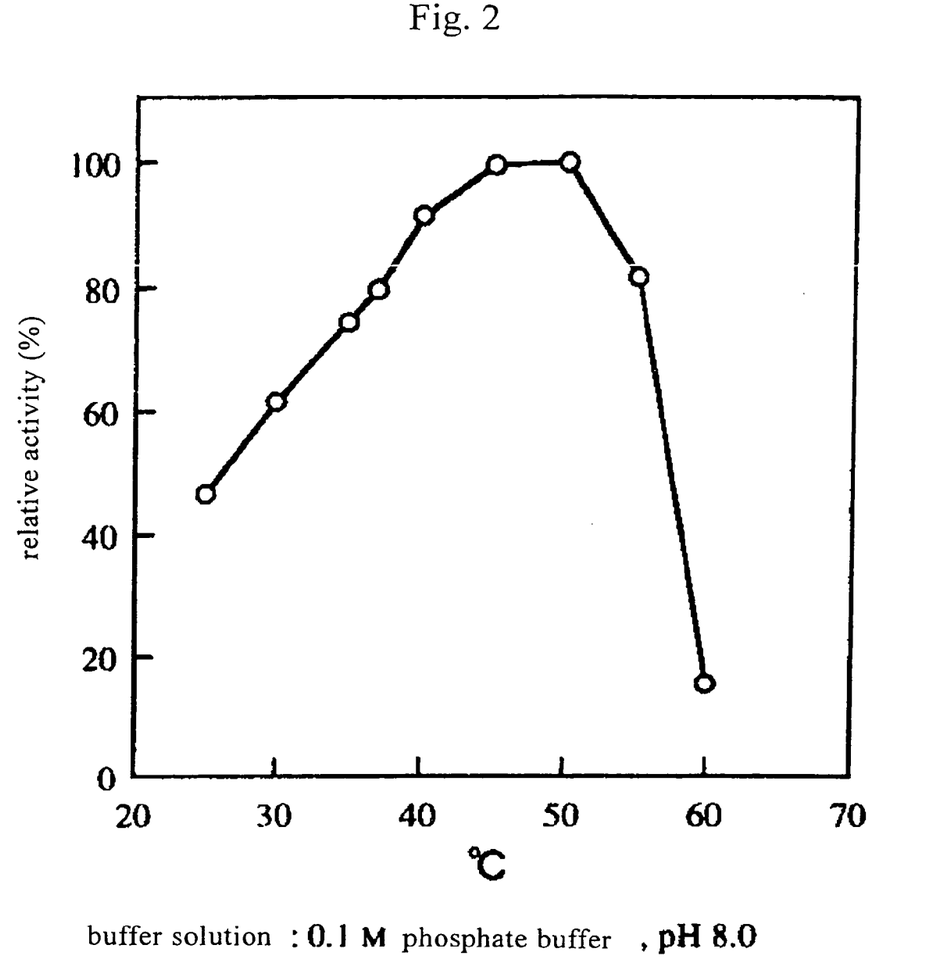
FIG. 2 shows the optimum temperature range for the action of the oxidase (Type 4) of the present invention.

Activity of the enzyme was measured at various temperatures using reaction solutions having the same composition as that of a reaction solution in the later-described method for measuring activity. Results were as shown in FIG. 2. As shown in FIG. 2, the optimum temperature for the action of the oxidase of the present invention ranged from 40 to 50° C.

(4) Stable pH range

Figure 3:
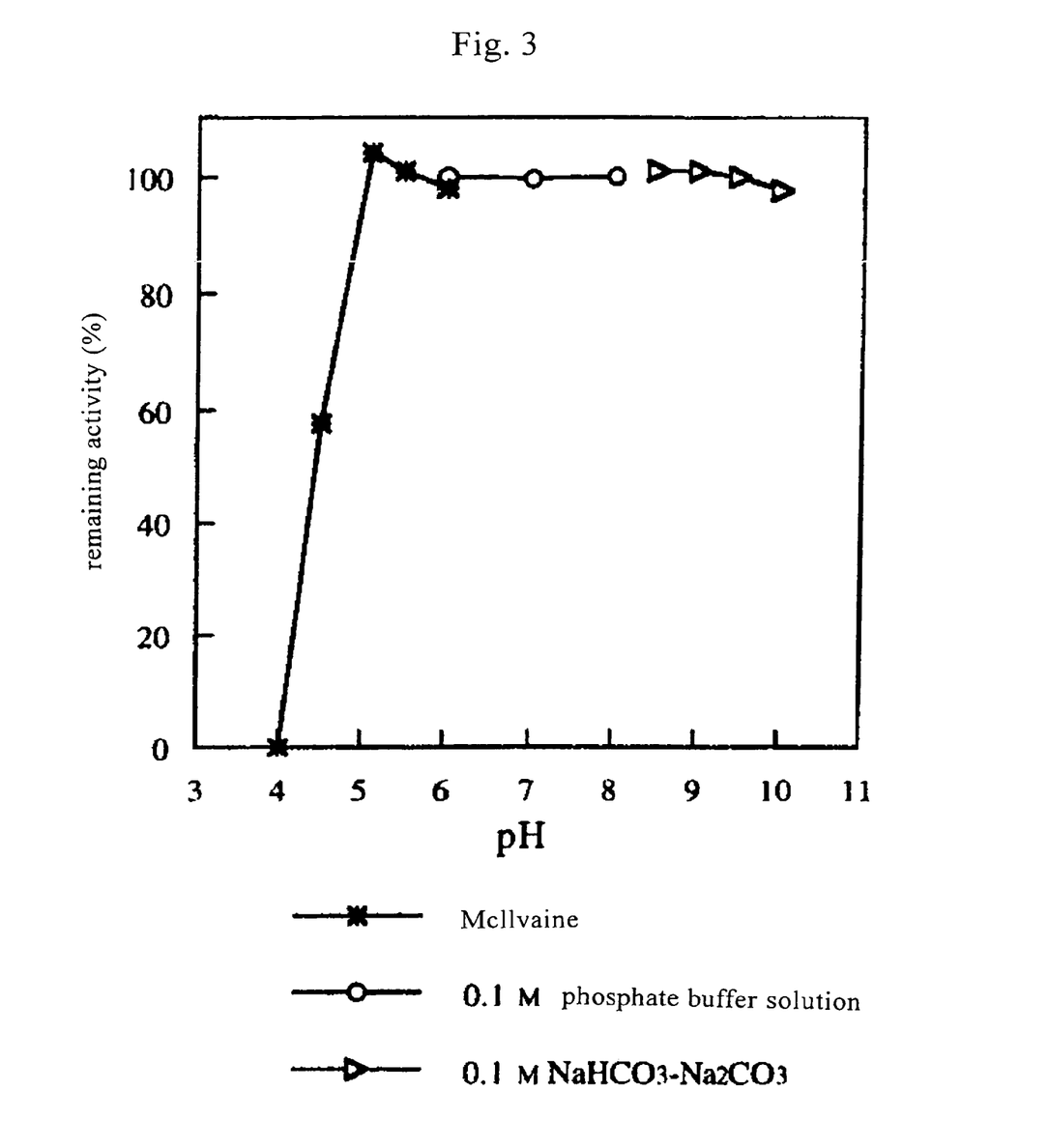
FIG. 3 shows the stable pH range for the oxidase (Type 4) of the present invention.

After treatment was performed at 37° C. for 10 minutes at each pH using as buffer solutions McIlvaine buffer solution (pH 3.0 to 6.0), 100 mM potassium phosphate buffer solution (pH 6.0 to 8.5), and 100 mM sodium hydrogen carbonate-sodium carbonate buffer solution (pH 8.5 to 10.0), the remaining activity of the oxidase of the present invention was measured. The resulting remaining activities were as shown in FIG. 3. As shown in FIG. 3, the stable optimum pH of the oxidase of the present invention ranged from pH 5.0 to 10.0.

(5) Thermal stability

Figure 4:
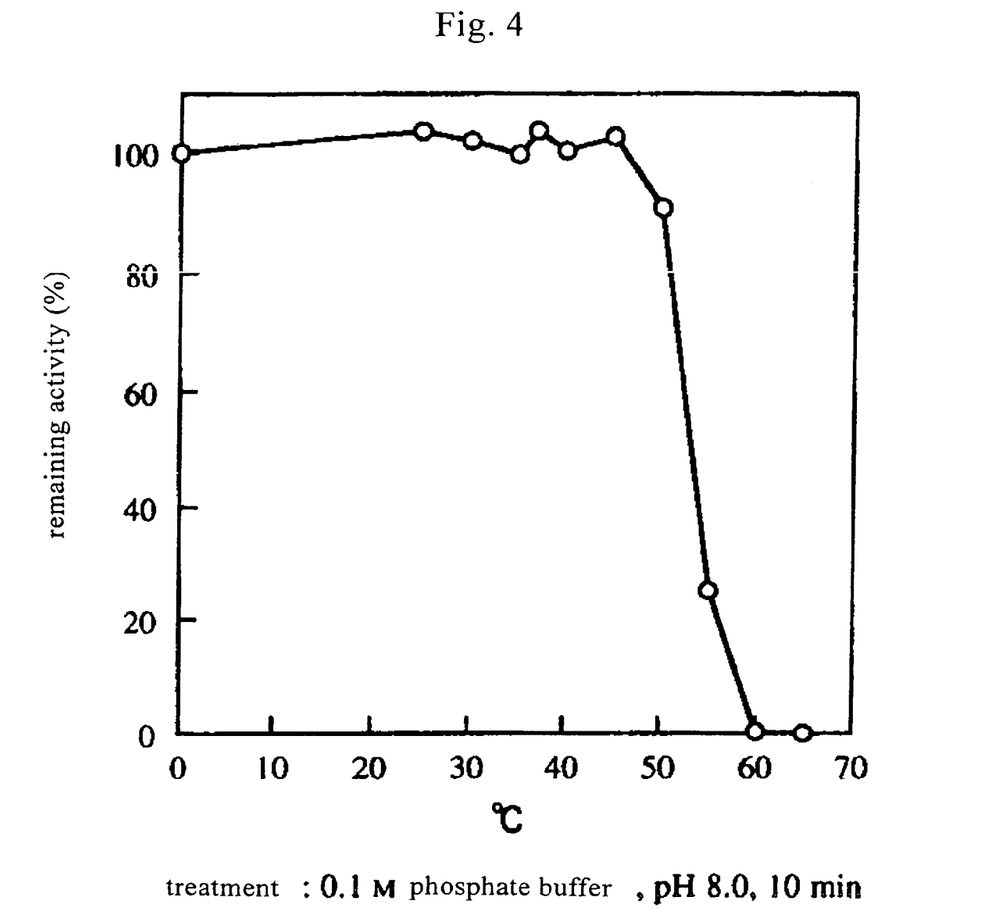
FIG. 4 shows the thermal stability of the oxidase (Type 4) of the present invention.

When treatment was performed at each temperature for 10 minutes using 100 mM potassium phosphate buffer solution (pH 8.0), the resulting thermal stabilities were as shown in FIG. 4. The oxidase of the present invention remained stable to temperatures around 45° C.

(6) Molecular weight

According to a standard method, molecular weight was found by a column gel filtration method (in 0.1 M sodium chloride-containing 50 mM potassium phosphate buffer solution) using Sephadex G-200, and by the SDS-PAGE method using multigel 10/20 (Daiichi Pure Chemicals). The molecular weight of the oxidase of the present invention was approximately 88,000 (determined by gel filtration method), or approximately 44,000 (determined by SDS-PAGE).

(7) Isoelectric point

The isoelectric point of the oxidase of the present invention was approximately pH 4.2 as measured by an isoelectric focusing method according to a standard method.

INDUSTRIAL APPLICABILITY

According to the present invention, there are provided a novel fructosyl amino acid oxidase having higher thermal stability when prescribed as an enzyme for clinical diagnosis in a reagent, a gene encoding the same, a recombinant DNA wherein the gene is inserted into a vector DNA, a transformant and the like containing the gene, and a process for producing the oxidase. Thus, the present invention is industrially useful.

This specification includes a part or all of the contents as disclosed in the specification of Japanese Patent Application Nos. 2000-360590, and 2001-243049, which are priority documents of the present application. All publications, patents and patent applications cited herein are incorporated herein by reference in their entirety.

The invention claimed is:

1. An isolated fructosyl amino acid oxidase having the following physicochemical properties:
   (a) action and substrate specificity: catalyzing a reaction to generate glyoxylic acid or α-ketoaldehyde, an α-amino acid and hydrogen peroxide by oxidizing iminodiacetic acid, or a derivative thereof, in the presence of oxygen, but not acting on ε-fructosyl lysine;
   (b) optimum pH range: 7.5 to 8.5;
   (c) stable pH range: 5.0 to 10.0;
   (d) optimum temperature range for action: 40° C. to 50° C.;
   (e) thermal stability: showing 80% or more remaining activity when heat treatment is performed for 10 minutes at 50° C.; and
   (f) molecular weight: approximately 88,000 (determined by gel filteration), and approximately 44,000 (determined by SDS-PAGE).

2. An isolated protein of (a) or (b) having fructosyl amino acid oxidase activity, wherein (a) is an isolated fructosyl amino acid oxidase of SEQ ID NO: 2; or (b) is an isolated protein comprising the amino acid sequence of SEQ ID NO: 2.

3. The protein of claim 2, wherein an amino acid residue at the position selected from the group consisting of the $60^{th}$, the $188^{th}$, the $244^{th}$, the $257^{th}$, and the $261^{st}$ with respect to amino acid sequence of SEQ ID NO: 2 is modified.

4. The protein of claim 3, wherein the residue $257^{th}$ serine is substituted with asparagine.

* * * * *